United States Patent [19]

Shubkin et al.

[11] Patent Number: 4,910,355

[45] Date of Patent: Mar. 20, 1990

[54] OLEFIN OLIGOMER FUNCTIONAL FLUID USING INTERNAL OLEFINS

[75] Inventors: Ronald L. Shubkin; Gerhard O. Kuehnhanss, both of Baton Rouge, La.

[73] Assignee: Ethyl Corporation, Richmond, Va.

[21] Appl. No.: 266,156

[22] Filed: Nov. 2, 1988

[51] Int. Cl.[4] .................................................. C07C 2/74
[52] U.S. Cl. ..................................... 585/255; 585/329; 585/510; 585/518; 585/525; 585/669
[58] Field of Search ............... 585/255, 329, 510, 518, 585/525, 669

[56] References Cited

U.S. PATENT DOCUMENTS

| 4,218,330 | 8/1980 | Shubkin | 585/255 |
| 4,300,006 | 11/1982 | Nelson | 585/525 |
| 4,420,646 | 12/1983 | Darden et al. | 585/525 |
| 4,434,309 | 2/1984 | Larkim et al. | 585/525 |

Primary Examiner—Curtis R. Davis
Attorney, Agent, or Firm—Joseph D. Odenweller

[57] ABSTRACT

Olefin oligomers having a lower pour point are obtained by forming a mixture of $C_{8-18}$ olefins containing 50–90 weight percent α-olefins and 10–50 weight percent internal olefins and oligomerizing this mixture using a Friedel Crafts catalyst (e.g. $BF_3$) and a promoter (e.g. n-butanol). The mixture of olefins can be formed from α-olefins (e.g. 1-decene) by subjecting the α-olefins to isomerization until 10–50 weight percent of the olefins are internal olefins.

12 Claims, No Drawings

OLEFIN OLIGOMER FUNCTIONAL FLUID USING INTERNAL OLEFINS

BACKGROUND

Alpha-olefin oligomers and their use as hydraulic fluids and synthetic lubricants (synlubes) are well known. U.S. Pat. No. 2,937,129 reports the oligomerization of $C_{5-14}$ α-olefins using a dialkyl peroxide catalyst to make a synlube. U.S. Pat. No. 3,113,167 describes an α-olefin oligomer process using a titanium halide and an aluminum compound.

The preferred catalysts for making α-olefin oligomers are Friedel Crafts catalysts such as $BF_3$, U.S. Pat. No. 3,149,178. Optimum properties are obtained starting with 1-decene although mixtures of α-olefins have been used, U.S. Pat. No. 3,330,883.

The preferred Friedel Crafts catalyst is $BF_3$. Pure $BF_3$ is not an effective oligomerization catalyst. A small amount of polar compound is necessary as a promoter. U.S. Pat. No. 3,382,291 describes the use of alcohol promoters such as decanol. Other reported promoters are modenite (hydrogen form), water, phosphoric acid, fatty acids (e.g. valeric acid), ketones, organic esters, ethers, polyhydric alcohols, silica gel and the like.

For use as synlubes the oligomer product is preferably a trimer or higher oligomer including mixtures thereof. Low viscosity synlubes are preferably 1-decene trimer. These have a viscosity at 100° C. of about 3.4–3.7 cSt (centistokes). By including a small amount (e.g. 2–10 weight percent) of tetramer the viscosity can be increased to a more desirable 3.7–4.1 cSt at 100° C.

It has been observed that all 1-decene trimer fractions are not the same even when made with the same catalyst. For example, use of a promoted (e.g. water, alcohol, etc.) $BF_3$ system to oligomerize 1-decene followed by (1) topping to remove monomer and dimer and (2) distillation of the topped oligomer to remove a trimer fraction and (3) hydrogenation of the trimer fraction will give a synlube which either meets or can be adjusted to meet the 4 cSt synlube viscosity specifications. However, even though the synlube exhibits the proper viscosity at −40° C. (e.g. 2000–3000 cSt) and 100° C. (e.g. 3.6–4.2 cSt), the synlube will frequently fail to meet the low temperature pour point specification. A satisfactory 4 cSt synlube should have a pour point of −65° C. or lower. Thus a need exists for a method for making an α-olefin synlube that will not only meet the required viscosity specifications but will also consistently exhibit a satisfactory pour point.

SUMMARY OF THE INVENTION

An olefin oligomer suitable for use as a synthetic lubricant (synlube) having an improved low temperature pour point can be made by forming a mixture of $C_{8-18}$ olefins, preferably $C_{10}$ olefins, containing about 50–90 weight percent α-olefins and about 10–50 weight percent internal olefins and contacting this mixture with a catalytic amount of a Friedel Crafts catalyst, preferably $BF_3$, and a catalyst promoter, preferably alcohol or water, at a temperature of about 10°–80° C., washing to remove catalyst, distilling to remove monomer and optionally dimer an hydrogenating to obtain a substantially saturated olefin oligomer. The resultant oligomer exhibits a pour point that is lower than the pour point obtained with a comparative α-olefin under the same oligomerization conditions.

DESCRIPTION OF THE PREFERRED EMBODIMENTS

A preferred embodiment of the invention is a process for making an olefin oligomer having a low pour point, said process comprising:

(A) forming a mixture of $C_{8-18}$ olefins in which about 50–90 weight percent of the olefins are α-olefins and 10–50 weight percent are internal olefins an (B) oligomerizing said mixture of olefins by contacting said mixture with a Friedel Crafts catalyst and a promoter for said catalyst at a temperature of about 10°–80° C. to form a mixture of dimer, trimer and tetramer containing minor amounts of monomer and oligomers higher than tetramer.

The oligomerization reaction can be conducted in a conventional manner. The starting olefin mixture should contain olefins containing 8–18 carbon atoms or mixtures of such olefins. The most preferred olefins are mainly $C_{10}$ olefins, preferably at least 80 weight percent $C_{10}$ olefins and more preferably about 90 weight percent $C_{10}$ olefins.

The prior art has taught that the preferred olefins for making synlubes are mainly α-olefins such as 1-decene. However, we have found that an oligomer having a lower pour point can be obtained using a mixture of α-olefins and internal olefins. This mixture should contain at least 10 weight percent internal olefins and preferably at least 20 weight percent internal olefins. We have found that the pour point continues to improve (i.e. decrease) moving up to 50 weight percent internal olefins although even higher amounts may show further improvement.

The initial olefin mixture may be obtained by physically mixing an α-olefin with an internal olefin in amounts to obtain the desired ratio. For example, mixing 60 Kg of 1-decene with 40 Kg of internally unsaturated decenes results in a very useful starting mixture.

In a preferred mode of operation the olefin mixture is made from a $C_{8-18}$ α-olefin or mixture of such α-olefins. Alpha-olefins are readily available in large volumes at reasonable cost. The α-olefins are then subjected to an isomerization reaction by contacting them with one or more of the well-known olefin isomerization catalysts under isomerization conditions until the desired amount of internal olefins are formed. Isomerization catalysts include iron carbonyl, $AlCl_3$, $BF_3$, $BCl_3$, $PdCl_2(PhCN)_2$, Pd/C, Ru/C, Rh/C, $Cr(CO)_6$, $Mo(CO)_6$, $SiO_2/Al_2O_3$, $SiO_2$, $Al_2O_3$. The isomerization can be conducted in a batch operation by placing a catalytic amount of the isomerization catalyst in the α-olefin and stirring the mixture at a temperature high enough to cause isomerization to proceed. A useful range is about 50°–300° C. When using iron carbonyl as the isomerization catalyst a preferred temperature range is 150°–260° C.

In another mode of operation, the isomerization can be carried out in a continuous process by passing the olefin through a catalyst bed in a packed column. This requires the use of a heterogeneous catalyst or a catalyst adsorbed on a suitable catalyst support.

In a highly preferred embodiment the isomerization catalyst is a Friedel Crafts type catalyst such as $BF_3$, $BCl_3$, $AlCl_3$, $AlBr_3$, $FeCl_3$, $ZnCl_4$, $ZnCl_2$, $GaCl_3$ and the like. These catalysts are used in the absence of the catalyst promoter required to cause oligomerization. Under these conditions they function to isomerize the olefins without causing any substantial amount of oligomerization.

In a still more preferred embodiment the Friedel Crafts isomeriztion catalyst is the same Friedel Crafts catalysts used in the subsequent oligomerization process. In this mode of operation the Friedel Crafts catalyst is placed in the initial α-olefin in an amount sufficient to cause isomerization. A useful amount is about 0.1–1.0 weight percent based on the α-olefin. The mixture is stirred at isomerization temperature, for example 50°–300° C., without adding a promoter. When the desired amount of internal olefins have formed, e.g. 10–50 weight percent and more preferably 20–50 weight percent, the temperature is adjusted to the desired oligomerization temperature, e.g. 10°–80° C. more preferably 20°–60° C., still more preferably 25°–50° C. and most preferably 30°–40° C. and the promoter; e.g. water, alcohol, fatty acid, fatty acid ester, ketone, ether, polyol, polyglycol and the like; added either all at once or over a period of time, e.g. 30 minutes to 1 hour. The oligomerization is then conducted until the desired degree of oligomerization is achieved. In general the criteria is to lower the monomer content below 5 weight percent and preferably below 2 weight percent. During this oligomerization reaction when using a volatile catalyst such as $BF_3$, it is desirable to conduct the oligomerization under pressure, for example 10–100 psig $BF_3$ pressure.

When starting with $C_{8-18}$ olefin mixture of internal and terminal olefins made by physically mixing the different olefins, the oligomerization is conducted in the usual manner by placing the α-olefin in a suitable corrosion-resistant reactor and contacting the olefin with a Friedel Crafts catalyst, preferably $BF_3$. This can be done in many ways such as by bubbling $BF_3$ through the α-olefin or placing the α-olefin under $BF_3$ pressure (e.g. 10–100 psig) in a closed reactor. A promoter for the $BF_3$ is then slowly added to the reaction mixture at a controlled rate. Any of the known $BF_3$ promoters can be used such as water, alcohol (isopropanol, n-butanol, 1-decanol, etc.), fatty acid (e.g. acetic acid, valeric acid, caproic acid, etc.), polyhydric alcohols (e.g. glycol, glycerol, etc.) ketones (e.g. acetone), aldehydes (e.g. butyraldehyde), acid anhydrides (e.g. acetic anhydride) and the like. A description of useful promoters is given in U.S. Pat. Nos. 3,149,178; 3,382,291; 3,742,082; 3,763,244; 3,769,363; 3,780,128; 3,997,621; 4,045,507 and elsewhere.

The most preferred promoters are water and alcohols (e.g. n-butanol).

The total amount of promoter should be a promoter amount. This can vary over a wide range, e.g. 0.1–2.0 weight percent based on olefin. A preferred amount is about 0.3–1.0 weight percent and a more preferred amount is 0.4–0.8 weight percent.

A highly preferred embodiment of the invention is the process for making a $C_{8-18}$ olefin oligomer having a low pour point by a process comprising:

(A) isomerizing a $C_{8-18}$ α-olefin or mixture thereof in the presence of a Friedel Crafts catalyst until about 10–50 weight percent of said α-olefin is converted to internal olefin forming an isomerized mixture, (B) adding a Friedel Crafts catalyst promoter to said isomerized mixture, (C) oligomerizing the isomerized mixture at a temperature of about 10°–80° C., (D) contacting the oligomerized reaction mixture with an aqueous wash to remove said Friedel Crafts catalyst, (E) distilling the washed reaction mixture to remove monomer and dimer leaving a topped unsaturated oligomer as a residual product and (F) hydrogenating said residual product to obtain a substantially saturated olefin oligomer.

As in the previous embodiments, the most preferred Friedel Crafts catalyst is $BF_3$ and the oligomerization reaction is conducted under $BF_3$ pressure. The preferred promoters are water and alcohol, especially n-butanol. A more preferred oligomerization temperature is 20°–60° C., more preferably 25°–50° C.

The aqueous wash to remove catalyst can be conducted with water or with an aqueous base such as water containing about 1–10 weight percent, NaOH, $Na_2CO_3$, KOH, $NH_4OH$, $NaHCO_3$ and the like. Multiple washes are frequently used to obtain more complete removal of the catalyst. These can be multiple water washes or multiple aqueous base washers. In one embodiment the initial wash is with aqueous base, e.g. 5 weight percent caustic, followed by one or more water washes.

Distillation to remove monomer and trimer can be conducted in a conventional manner. Preferably the distillation is conducted under vacuum, especially with $C_{10}$ and higher olefin oligomers. In one preferred mode the unreacted monomer can be distilled at atmospheric pressure and the pressure is reduced for dimer removal to prevent decomposition of the oligomer.

If the desired product is a 4 cSt synlube, the vacuum distillation can be continued to recover a trimer fraction having an exceptionally low pour point. Higher viscosity synlubes, e.g. 6 cSt synlubes, can be obtained by using the entire residual product after dimer removal and, if necessary, partial trimer removal. To obtain a still higher viscosity synlube, e.g. 8 cSt synlube, the distillation is continued to remove a larger portion of trimer until the desired viscosity is achieved.

The distilled trimer or the distillation residue can then be hydrogenated by conventional means using a hydrogenation catalyst at 100°–300° C. under 100–1000 psig $H_2$ pressure. A very useful and relatively inexpensive catalyst for this use is nickel on a support such as kieselguhr. The hydrogenation may be conducted in a batch process or by a continuous process such as the conventional trickle-bed hydrogenation in which the unsaturated oligomer is passed down through a column packed with supported hydrogenation catalyst while hydrogen is passed upwardly through the column countercurrent to the oligomer all at 200°–300° C.

The following examples show how the process is carried out and also show the decrease in pour point achieved by the new process.

EXAMPLES 1–5

These examples were conducted by placing the olefin and promoter in a reaction vessel and stirring the mixture at 30° C. with excess $BF_3$ bubbling through the reactor. The oligomerization was conducted for about 120 minutes. The reaction mixture was then water washed and distilled to remove monomer and dimer. For a better indication of the affect of internal olefins on the course of the reaction, the trimer fraction from each example was recovered by fractional distillation. The viscosity and pour point was determined on the trimer fractions after hydrogenating at 250° C., 800–900 psig H$_2$ using a nickel catalyst. The olefins used were 1-decene and internal decene. The following table shows the reaction conditions, viscosities and pour points of the product.

| | Example | | | | |
|---|---|---|---|---|---|
| | 1 | 2 | 3 | 4 | 5 |
| 1-decene (%) | 100 | 100 | 90 | 80 | 50 |
| int. decene (%) | 0 | 0 | 10 | 20 | 50 |
| promoter | H$_2$O | n-buOH | n-buOH | n-buOH | n-buOH |
| viscosity (cSt) −40° C. | 2,240 | 2,330 | 2,140 | 2,240 | 2,980 |
| viscosity (cSt) 40° C. | 17.3 | 15.5 | 15.5 | 17.2 | 17.1 |
| viscosity (cSt) 100° C. | 3.72 | 3.62 | 3.62 | 3.67 | 3.76 |
| pour point (°C.) | −54 | −54 | −57 | −66 | <−69 |

The results show that at 10 weight percent internal olefin the drop in pour point is first observed and at 20 weight percent internal the decrease in pour point is more than 10 degrees compared to the oligomer made using only 1-decene.

We claim:

1. A process for making a C$_{8-18}$ olefin oligomer having a low pour point, said process comprising:
   (A) isomerizing a C$_{8-18}$ α-olefin or mixture thereof in the presence of a Friedel Crafts catalyst until about 10–50 weight percent of said α-olefin is converted to internal olefin forming an isomerized mixture,
   (B) adding a Friedel Crafts catalyst promoter to said isomerized mixture,
   (C) oligomerizing said isomerized mixture at a temperature of about 10°–80° C.,
   (D) contacting the oligomerized reaction mixture with an aqueous wash to remove said Friedel Crafts catalyst,
   (E) distilling the washed reaction mixture to remove monomer and dimer leaving a topped unsaturated oligomer as a residual product and
   (F) hydrogenating said residual in the presence of a hydrogenation catalyst to obtain a substantially saturated olefin oligomer.

2. A process of claim 1 wherein said Friedel Crafts promoter is BF$_3$.

3. A process of claim 2 wherein step (c) is conducted under BF$_3$ pressure.

4. A process of claim 3 wherein said α-olefin is at least 80 weight percent 1-decene.

5. A process of claim 4 wherein said promoter is water or alcohol.

6. A process of claim 5 wherein said promoter is n-butanol.

7. A process for making a C$_{8-18}$ olefin oligomer having a low pour point, said process comprising:
   (A) isomerizing a C$_{8-18}$ α-olefin or mixture thereof in the presence of a Friedel Crafts catalyst until about 10–50 weight percent of said α-olefin is converted to internal olefin forming an isomerized mixture,
   (B) adding a Friedel Crafts catalyst promoter to said isomerized mixture,
   (C) oligomerizing said isomerized mixture at a temperature of about 10°–80° C. and
   (D) contacting the oligomerized reaction mixture with an aqueous wash to remove said Friedel Crafts catalyst.

8. A process of claim 7 wherein said Friedel Crafts catalyst is BF$_3$.

9. A process of claim 8 wherein said α-olefin is at least 80 weight percent 1-decane.

10. A process of claim 9 wherein the oligomerized reaction mixture is distilled to remove monomer and dimer leaving a topped unsaturated oligomer as a residual product.

11. A process of claim 10 wherein said promoter is water or alcohol.

12. A process of claim 11 wherein said promoter is n-butanol.

* * * * *